United States Patent
Augustine et al.

(10) Patent No.: US 6,497,720 B1
(45) Date of Patent: *Dec. 24, 2002

(54) SUPPORT APPARATUS WITH A PLURALITY OF THERMAL ZONES PROVIDING LOCALIZED COOLING

(75) Inventors: Scott D. Augustine, Bloomington, MN (US); Paul Anthony Iaizzo, White Bear Lake, MN (US); Ephraim M. Sparrow, St. Paul, MN (US); Paul Steven Johnson, White Bear Lake, MN (US); Randall C. Arnold, Minnetonka, MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/758,062

(22) Filed: Jan. 10, 2001

Related U.S. Application Data

(63) Continuation of application No. 09/473,325, filed on Dec. 28, 1999, which is a continuation of application No. 09/020,079, filed on Feb. 6, 1998, now Pat. No. 6,033,432, which is a continuation of application No. 08/707,967, filed on Aug. 30, 1996, now Pat. No. 5,800,480.

(51) Int. Cl.[7] .................................................. A61F 7/00
(52) U.S. Cl. ........................ 607/96; 607/107; 607/112
(58) Field of Search ........................... 607/46, 104, 107, 607/108, 112; 297/452.13, 452.41, 452.42, 180.14, 180.16; 5/421, 423, 724, 726; 126/205

(56) References Cited

U.S. PATENT DOCUMENTS

| | | |
|---|---|---|
| 3,289,748 A | 12/1966 | Jennings |
| 3,738,702 A | 6/1973 | Jacobs .......................... 165/105 |
| 3,757,366 A * | 9/1973 | Sacher .................... 297/180.13 |
| 4,026,299 A | 5/1977 | Sauder ......................... 128/400 |
| 4,114,620 A | 9/1978 | Moore et al. ................. 128/254 |
| 4,149,541 A | 4/1979 | Gammons et al. ........... 128/400 |
| 4,416,281 A | 11/1983 | Cooper et al. ............... 128/400 |
| 4,706,672 A | 11/1987 | Jones ........................... 128/379 |
| 4,788,730 A * | 12/1988 | Bexton ........................... 5/454 |
| 4,844,072 A | 7/1989 | French et al. ................ 128/400 |
| 4,884,304 A | 12/1989 | Elkins ............................. 5/421 |
| 4,886,063 A * | 12/1989 | Grews ......................... 607/112 |
| 4,962,761 A | 10/1990 | Goldent ....................... 128/400 |
| 4,966,145 A | 10/1990 | Kikumoto et al. ........... 128/377 |
| 5,072,875 A | 12/1991 | Zacoi ........................... 128/400 |
| 5,097,829 A | 3/1992 | Quisenberry ................ 128/400 |
| 5,138,138 A | 8/1992 | Theilacker et al. .......... 219/528 |
| 5,169,384 A | 12/1992 | Bosniak et al. ................ 604/20 |
| 5,174,285 A | 12/1992 | Gontenot ..................... 128/400 |
| 5,176,424 A | 1/1993 | Tobita et al. ................. 297/284 |
| 5,183,039 A | 2/1993 | Sarian et al. ................ 128/400 |
| 5,269,369 A | 12/1993 | Faghri ......................... 607/104 |
| 5,344,436 A | 9/1994 | Fontenot et al. ............ 607/104 |
| 5,433,083 A | 7/1995 | Kuramarohit ................. 62/259 |
| 5,448,788 A | 9/1995 | Wu ................................. 5/421 |
| 5,456,701 A | 10/1995 | Stout ........................... 607/104 |
| 5,486,206 A | 1/1996 | Avery .......................... 607/104 |
| 5,800,480 A * | 9/1998 | Augustine et al. ....... 607/108 X |
| 6,033,432 A * | 3/2000 | Augustine et al. ............ 607/96 |
| 6,263,530 B1 * | 7/2001 | Feher .......................... 165/185 |

* cited by examiner

*Primary Examiner*—Linda C. M. Dvorak
*Assistant Examiner*—Kenneth G Schopfer
(74) *Attorney, Agent, or Firm*—Gray Cary Ware & Freidenrich; Terrance A. Meador

(57) ABSTRACT

An apparatus for supporting a human or animal body, while selectively cooling weight-bearing areas of the body in order to prevent or reduce damage from ischemia includes a cooling layer that is partitioned into a plurality of zones, and a surface disposed over the cooling layer to support the body. Each zone of the cooling layer is disposed for cooling a respective portion of the surface. Means are provided to selectively operate one or more zones of the plurality of the zones to cool a portion of the surface that receives pressure from a weight-bearing surface of the body being supported.

9 Claims, 5 Drawing Sheets

SUPPORT APPARATUS WITH A PLURALITY OF THERMAL ZONES PROVIDING LOCALIZED COOLING

This application is a continuation of U.S. patent application Ser. No. 09/473,325, filed Dec. 28, 1999, which was a continuation of U.S. patent application Ser. No. 09/020,079, filed Feb. 6, 1998 (now U.S. Pat. No. 6,033,432), which was a continuation of U.S. patent application Ser. No. 08/707,967, filed Aug. 30, 1996 (now U.S. Pat. No. 5,800,480).

BACKGROUND OF THE INVENTION

1. Field of the Invention

The invention concerns an apparatus for supporting at least a portion of a human or animal body with cooling localized at or focused on the weight-bearing areas of the portion. The localized, or focused, cooling reduces the risk of damage to the weight-bearing body areas of patients confined to beds or wheelchairs for long periods of time.

The application of pressure to the skin of a patient for a prolonged period of time has been known to cause pressure ulcers or pressure ulcers. The weight-bearing areas of the body surface are exposed to pressures that can easily exceed 100 mmHg (torr.). It has been shown that blood flow ceases in capillaries that are exposed to compressive pressures exceeding 25 torr. Therefore, the weight-bearing areas of the body surface and subcutaneous tissue can be expected to have inadequate blood flow or even a complete lack of blood flow during the time the weight is borne.

Normal cellular metabolism depends on adequate circulation of blood to deliver oxygen, nutrients and to remove waste products. Prolonged interference with the local circulation results in a two-part sequence of events, beginning with ischemia (a severe reduction of blood and oxygen supply to the tissues), and terminating in necrosis (irreversible death of the cells and tissues, resulting in sloughing).

People normally will shift their positions in a chair or get up and walk around to relieve the pressure on their buttocks. People normally will regularly roll over in bed while sleeping to periodically redistribute their weight to a different surface area. This movement is usually in response to pain or discomfort caused by the tissue ischemia of the weight-bearing skin, subcutaneous or deeper tissue. Bed-ridden or wheelchair-ridden patients or patients on operating tables may not be aware of the ischemic pain if they have brain or spinal cord injury, stroke injury, dementia, prolonged surgery under anesthesia, or prolonged sedation and mechanical ventilation. Alternatively, severe illness, neuro-muscular diseases or nervous system injury may prevent patients from moving even if they are aware of the ischemic pain.

The incidence of pressure ulcers in surgical patients varies from 12% to 66% in different studies. Surveys of general hospital patients indicate that 3–4.5% of all patients develop pressure ulcers during hospitalization. Pressure ulcers usually develop near regions of the body which have a bony prominence near the skin. More than 80% of all pressure ulcers occur at the following five locations:

1. Sacro-coccygeal region (high buttocks), supine position.
2. Greater trochanter (low hip), lateral recumbent position.
3. Ischial tuberosity (low buttocks), sitting position.
4. Tuberosity of the calcaneus (heel), supine position.
5. Lateral malleolus (outer ankle), lateral recumbent position.

Surgical and bed ridden patients are not the only patients susceptible to pressure ulcer development. For example, paralyzed patients spend much of their lifetime in a wheelchair. One study indicated that the incidence of pressure ulcers is 21.6% for paraplegics and 23.1% for quadriplegics.

Equipment for pressure ulcer prevention has focused in three areas:

1. Regular turning or movement of the patient to minimize the duration of time that pressure is applied to any give surface area The tissue is allowed time to re-perfuse during the period that the pressure is not applied.
2. Passive support surfaces (cushions, mattresses and pads of all kinds), which may utilize unique or special materials or shapes to minimize the pressure exerted against any given point of the body surface. Many types of materials have been tried including; different types of polymeric foam, polymeric gels, water and air filled bladders.
3. Active support surfaces such as a series of air filled bladders that alternately inflate and deflate to automatically redistribute the pressure.

Considering the high incidence of pressure ulcers despite the availability of these many passive support surfaces (various materials and shapes), it is clear that simply distributing the pressure to a larger surface area, in and of itself, will not effectively prevent pressure ulcers. Although active support surfaces have been used to prevent pressure ulcers, it is clear however that they are very expensive, cumbersome and noisy. Therefore active support surfaces are not likely to be used in the majority of pressure ulcer prevention situations.

Finally, aside from the obvious pain and health risk to the patient (having a chronic infection in a chronic open wound), pressure ulcers are extremely expensive and slow to heal. Healing the average pressure ulcer costs $30,000 to $40,000 and takes about 3 to 6 months. The high incidence of pressure ulcers, the lack of any proven method of preventing pressure ulcers and the extremely high cost of healing a pressure ulcer once it develops, clearly indicates a significant need for a new technology.

It is reasonable to assume that heat should be an important factor in the formation of pressure ulcers. All tissues increase their metabolic rates 7–10% for each 1° C. increase in temperature. The increased metabolic rate increases the demand of the cells for oxygen a similar 7–10% for each 1° C. increase in temperature. In a patient whose tissue perfusion is already compromised by external pressure or by vascular insufficiency, this increased metabolic demand for oxygen could increase the rate of tissue injury. We hypothesized that this increased metabolic demand was the cause of the frequent "bums" observed after water mattress warming therapy during surgery, despite the relatively low temperatures (39°–42° C.) of the mattresses. These low temperature injuries may result in full thickness skin damage which appears identical to third degree burns resulting from exposure of the skin to high temperatures. While the full thickness damage to the skin is identical to a high temperature thermal injury ("burn"), in reality the injury is caused by pressure necrosis which is accelerated due to the increased metabolic rate of the tissue. While this interrelationship between temperature, pressure and tissue ischemia is scientifically logical, it had never been proven prior to our recent experiments.

Further, it is known that hypothermia decreases the cellular metabolic rate and increases the tolerance of cells to periods of inadequate blood flow. This is the reason that patients are cooled during cardiac bypass. We therefore hypothesized that cooling the skin and subcutaneous tissue would effectively prolong the time to injury, in the face of the ischemia caused by an inadequate local blood flow resulting from pressure exerted against that tissue.

To test these hypotheses, we developed a porcine model to investigate pressure ulcer formation. Twelve metal discs were applied to the back of an anesthetized swine. The pressure on the skin under each disc was approximately 100 torr (totally occlusive to blood flow), for a 10 hour period of time. The temperature of the discs was carefully controlled at 25° C., 35° C., 40° C. and 45° C. Normal porcine temperature is 38° C. (Normal human body temperature is 37° C.) The severity of the resultant tissue injuries directly correlated with an increase in temperature. No tissue damage was found under the 25° C. discs. Severe damage of the skin, subcutaneous and deep tissues was found under the 45° C. discs. The 35° and 40° C. discs also caused severe damage, but intermediate to the extreme temperatures. The results of this experiment strongly indicate that both of our hypotheses were correct:

1. Even mild heat will accelerate the rate of tissue injury due to pressure induced ischemia
2. Mild cooling will protect tissue from injury due to pressure induced ischemia.

Water mattresses circulating cool or even cold water have been used for decades to cool febrile patients. However, experience shows that the application of cold to widespread surface areas of the body is both extremely uncomfortable and will cause hypothermia and shivering.

2. Description of the Related Art

In the prior art, U.S. Pat. No. 3,738,702 discloses a seat structure that cools a portion of the human body that rests against the seat in response to the heat of the body, where the body engages the seat. In order to maximize the sensitivity of the cooler to body heat, the cooler is placed as near as possible to the surface of the seat contacted by the body.

SUMMARY OF THE INVENTION

The object of this invention is to provide an article such as a bed mattress, or a chair or wheelchair cushion having a surface for supporting at least a portion of a human or animal body ("body portion"). According to this invention, specific areas of "high" pressure contact of the body portion between the surface and the skin of the body portion (greater than 20–25 torr.) are selectively cooled to remove heat from those specific areas.

In supine or sitting patients, metabolic heat generated by the ischemic tissue is trapped by insulating cushions and raises the tissue temperature. The metabolic heat cannot be internally removed because of the inadequate blood flow and cannot be externally removed because of the thermal insulation characteristics of the padded cushions or mattresses. The metabolism continues (anaerobically) despite the inadequate blood flow and the heat generated by this metabolism continues to accumulate. Our swine studies show that any warming of tissue is clearly harmful and cooling of the tissue below body temperature is beneficial in preventing pressure injury to tissue. Cooling below normal body temperature will be beneficial. Therefore this invention prevents the buildup of naturally generated metabolic body heat in the ischemic tissue. The adjacent body surface areas which are not experiencing high pressure will not be cooled. Because of the minimal blood flow in the areas of high pressure, the cooling effect will be substantially isolated to those tissues and not cause total body hypothermia or discomfort.

Our invention is based upon the critical observation that those areas of the body that are subject to the greatest risk of ischemia in bearing the weight of the body may have cooling selectively applied by an apparatus that is subdivided or partitioned to into zones, with each zone capable of applying cooling to a weight-bearing surface. According to an optional element, such cooling may be provided by manual selection, or automatically, in response to the pressure exerted on a support surface by a human or animal body. Those areas of the body which exert the greatest pressure against the surface (the weight-bearing areas) are identified either by sight or by measurement of the pressure, and the portions of the surface contacted by the weight-bearing areas are cooled by activation of one or more contiguous cooling zones. The cooling applied to a support surface portion also cools a weight-bearing area that applies pressure to the portion.

The zones can be selected manually by the caregiver. Optionally a pressure sensing means can be provided to sense the contact pressure between the support surface and the skin of the body being supported. When a threshold contact pressure is surpassed, the sensing means activates a means which automatically initiates cooling by way of one or more zones adjacent to portions of the surface where weight-bearing areas are supported.

With greater specificity, our invention is an apparatus that localizes cooling applied to a supported human or animal body by selectively activating cooling zones disposed in alignment with those areas of the body bearing the body's weight.

DETAILED DESCRIPTION OF THE PREFERRED EMBODIMENTS

Figure 1:
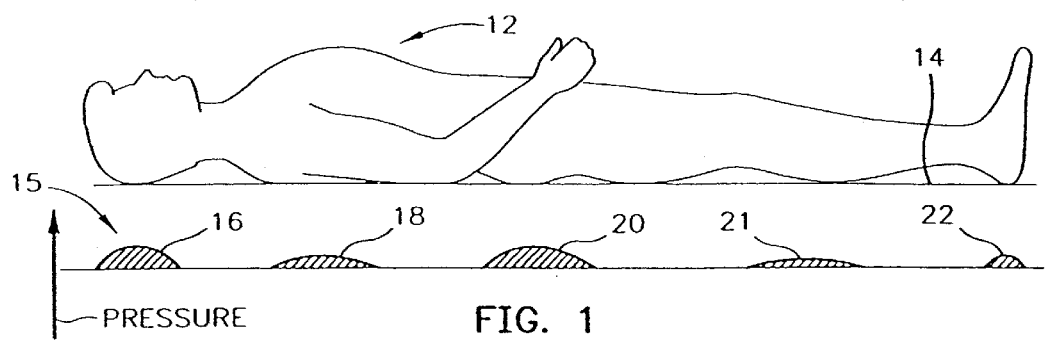
FIG. 1 illustrates a supine person and a plot showing pressure exerted on weight-bearing portions of the person's body by a surface that supports the body.

With reference now to the figures which illustrate this invention and in which like parts are designated by like reference numerals throughout the drawings, FIG. 1 shows a supine person 12 resting on, which is to say supported by, a surface 14. Directly underneath the surface 14 is a plot 15 that represents pressure measured at the surface 14. The pressure is exerted by the weight-bearing portions of the body and has its peak magnitude in those areas where the body 12 contacts the surface 14. Note particularly that distinct pressure profiles are exhibited for the back of the head at 16, the upper back at 18, the buttocks at 20, the calves at 21, and the heels at 22. (The contributions of the elbows are not shown.) These are the areas of the body which bear much of the weight of the person, and they are referred to as "weight-bearing" areas. Manifestly, if the supine person 12 is bed-ridden, the weight-bearing areas that include the buttocks and heels are at most risk for pressure injury.

The invention, in its structure and operation, provides localized cooling to alleviate the effects of pressure acting between a support surface and the weightbearing areas of a human or animal body. Localized cooling is provided by selectively operating zones of a multi-zone cooling layer to cool one or more portions of the support surface where weight-bearing areas of a supported human or animal body are borne, which consequently cools the weight-bearing areas. This principle is embodied preferably in an apparatus illustrated by the partially schematic cross-sectional drawings of FIGS. 2–4.

Figure 2:
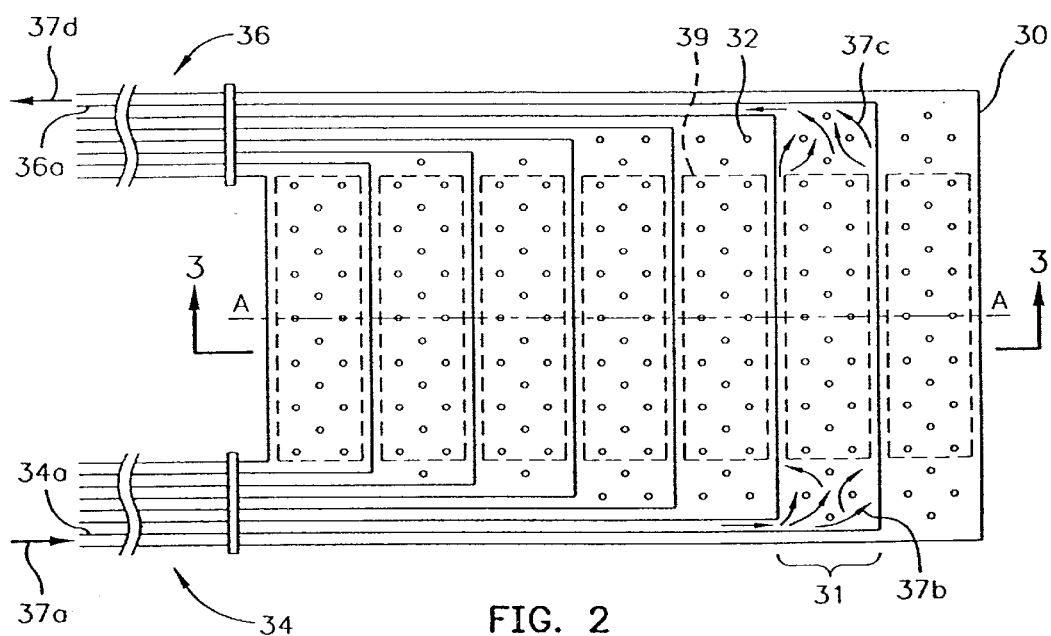
FIG. 2 is a top plan, partially schematic view of a preferred embodiment of the invention showing subdivision of a cooling layer into a plurality of zones.
Figure 3:
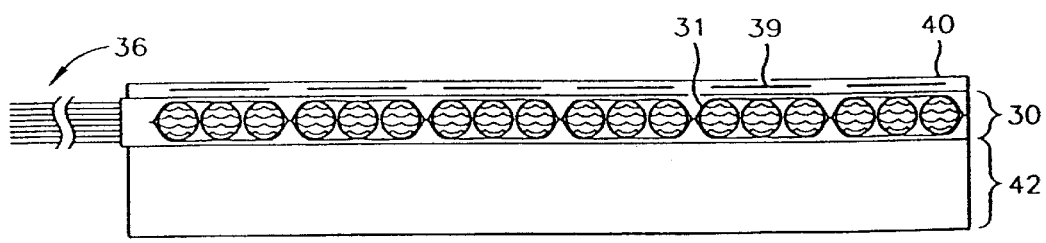
FIGS. 3 and 4 are longitudinal sectional, partially schematic illustrations of the preferred embodiment of FIG. 2.
Figure 4:
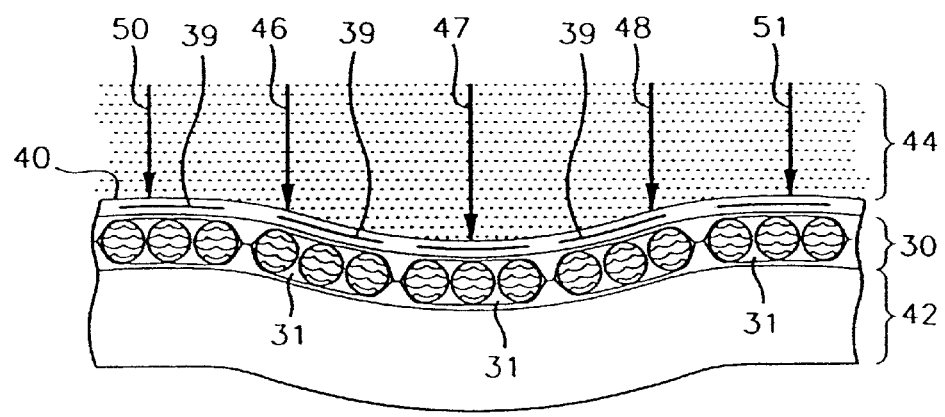

As FIGS. 2–4 illustrate, the invention includes a cooling layer 30 that is divided into a plurality of zones, such as the zone 31. FIG. 2 shows a top plan view of the cooling layer 30 with seven zones, one of which is the zone designated by the reference numeral 31. Preferably each of the zones comprises a separate chamber of a flexible water mattress through which cooled water, below 37° C. (normal human temperature), can be circulated, independently of any other chamber. Preferably, the chambers are rectangularly-shaped and each is comprised of one or more serpentine fluid channels formed by stake-point seals (such as the seal 32) that locally bond two sheets of material together. Each chamber has its own respective inlet hose and outlet hose, the inlet hoses for all chambers being indicated by reference numeral 34 and the outlet hoses by reference numeral 36.

In order to understand how each of the zones in the cooling layer 30 of the preferred embodiment operates, refer in particular to the zone 31. The chamber of which the zone 31 is comprised receives a respective flow of cooled water through the inlet hose 34a and returns the respective flow of cooled water through the outlet hose 36a. With this structure, an inlet flow of cooled water 37a is conducted to the zone 31 through the inlet hose 34a. Upon entry into the chamber of the zone 31, the inlet flow divides among the serpentine channels as indicated by 37b. The cooled water flows through the chamber of the zone 31, exiting as indicated by 37c into the outlet hose 36a.

While the term "water mattress" is used in the description of this preferred embodiment, it should be understood that many different fluids could be circulated through a corresponding structure with a similar cooling effect. Such fluids include, for example, glycol-water mixtures, alcohol-water mixtures, air, etc.

In the preferred embodiment of FIGS. 2–4, the water mattress that embodies the cooling layer 30 is divided into rectangular zones, with the longitudinal axis of each zone oriented substantially transversely with respect to the longitudinal axis A—A of a human body. In a mattress incorporating this embodiment of the cooling layer 30, each chamber would preferably be in its transverse dimension at least half the width of the mattress. This permits cooling of a transverse segment of the body which is in high pressure contact with a support surface 40, without cooling adjacent, normally perfused, contact areas of the body, which could lead to general hypothermia and discomfort. This however is not intended to limit the subdivision of the cooling layer 30 into a parallel array of elongate, rectangular zones; indeed, the zones could be square or rectangular in shape and distributed within the cooling layer in a checker-board pattern.

In the preferred embodiment illustrated in FIGS. 2–4, the fluid flow to each chamber is independently controlled. In this regard, the fluid flow can be manually controlled by a caregiver, or each chamber may have a corresponding pressure sensor to automatically initiate the flow of cooled fluid into, and through, that chamber when the pressure applied by the supported body against the support surface 40 exceeds a preselected threshold value. The preferred pressure sensing means in the embodiment illustrated in FIGS. 2–4 comprise a piezoresistive pressure-sensitive film that is incorporated into a structure or member that includes or is contiguous with the support surface. In the form of the preferred embodiment that comprises the elongated rectangular zones such as the zone 31, the piezoresisitive pressure-sensitive film would have formed in it respective individual piezoresisitive pressure-sensitive areas that are illustrated in dashed outline in FIG. 2. One such piezoresistive pressure-sensitive area is indicated by reference numeral 39. Each of these areas comprises a respective pressure sensor. As FIGS. 2–4 illustrate, the pressure sensor 39 comprises an elongated rectangular outline that is aligned, in plan, with the zone 31. As best seen in FIGS. 3 and 4, each pressure sensor is aligned, as described above, with respect to a respective zone. FIG. 3 shows a preferred structure for a mattress or a cushion that incorporates a support layer 42, preferably comprising a compressible material or structure in the form of a mattress.

In the structure illustrated in FIG. 3, the cooling layer 30 is in the form of a water mattress that can be similar in construction to a standard water mattress which is well known to the medical industry and may be obtained, for example, from Cincinnati Sub Zero Products, Cincinnati, Ohio, or Gaymar Industries, Orchard Park, N.Y., with the added feature of multiple, independent, preferably transverse fluid chambers. These mattresses are usually made of two sheets of flexible polyethylene polyvinyl film, thermal formed into a labyrinth of fluid channels, and then heat sealed together. Water is circulated through such a mattress by an external pump with cooling capabilities. Circulating cooled water causes the water mattress to be a primary heat sink. The heat is ultimately dissipated into a secondary heat sink which is usually ambient air. Connecting the primary and the secondary heat sink may require, in addition to the pump, a reservoir and a cooling means, all of which are conventional and not shown individually in the figures. The cooling means can be compression-based refrigeration cooling, thermoelectric based refrigeration cooling, radiator-based, ice-based, phase-change-material based, or based on any other suitable method that will maintain the circulating fluid at a temperature below the normal human body temperature 37° C.

As FIG. 3 shows, in the mattress or pad structure, the cooling layer is located just beneath the surface 40 that supports at least a portion of a human or animal body. Optionally, the structure that includes the surface 40 may also integrate the pressure sensors 39, so that the pressure sensors lie between the surface 40 and the cooling layer 30. This is not intended to foreclose a structure in which the sensors 39 are disposed over or on the surface 40. The sensors 39 also could be located beneath the cooling layer 30.

In FIG. 4, the shaded area 44 represents a portion of the human body supported on the surface 40. Assuming that the lengths of the arrows 46, 47 and 48 represent pressure exerted against the surface 40 by a weight-bearing portion of the body, such as the buttocks, and assuming further that pressure magnitudes represented by the lengths of those arrows exceed the magnitudes represented by the arrows 50 and 51, in the preferred embodiment cooled fluid is provided to the zones 31 that are aligned with the weight-bearing portion of the body indicated by the pressure profile 46, 47, 48.

Figure 5:
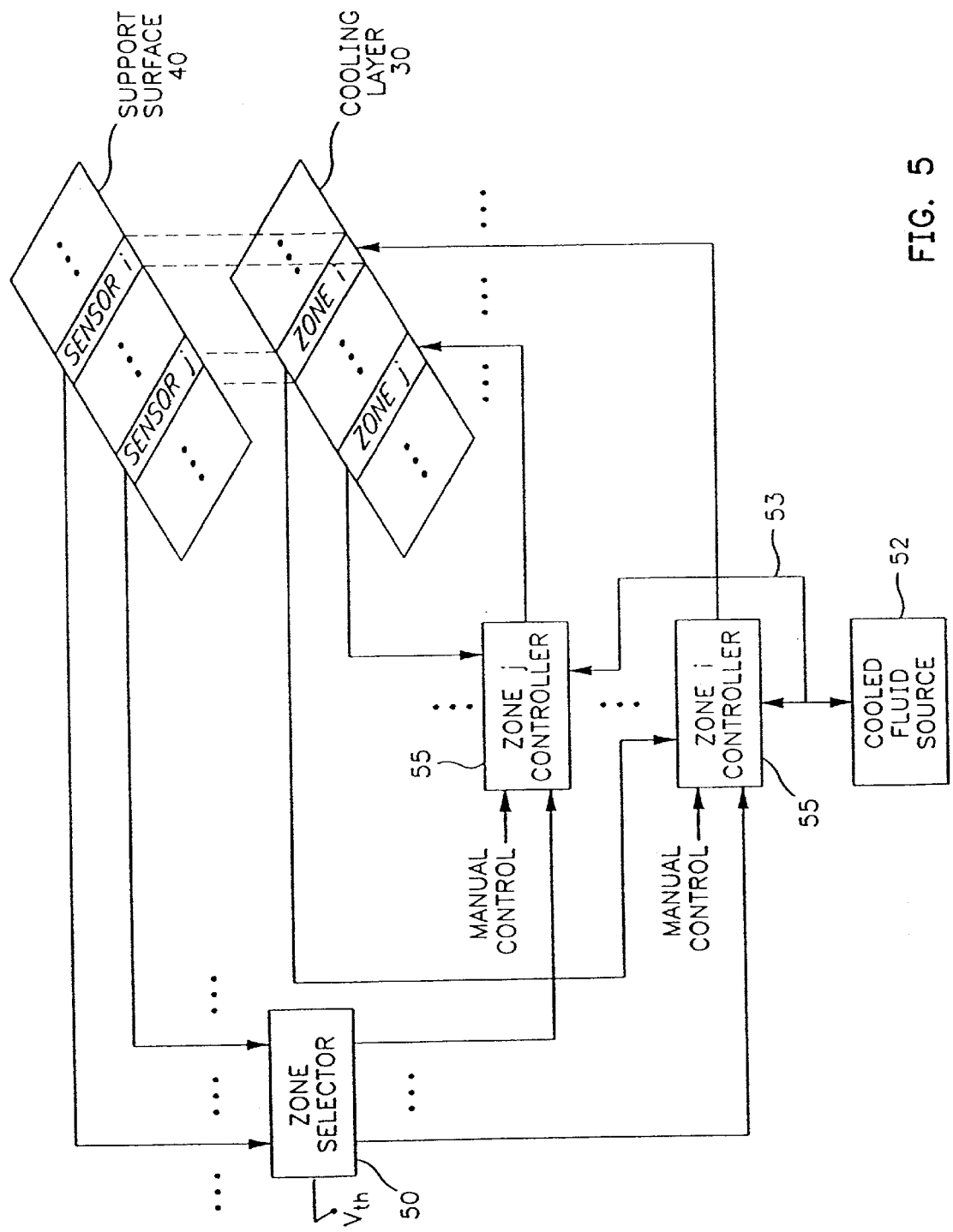
FIG. 5 is a schematic diagram showing control of the cooling zones of the preferred embodiment illustrated in FIG. 2.

Means for selectively operating one or more zones of the plurality of zones in the cooling layer 30 to cool a portion of the surface 40 that receives pressure from a weight-bearing area of the body represented by shaded area 44 are illustrated in FIG. 5. In FIG. 5, the array of pressure sensors 39 including pressure sensor$_i$ and pressure sensor$_j$ provide indications of pressures exerted against the surface 40 by a human or animal body. Preferably, the pressure sensors provide voltage signals that are compared against a threshold voltage $V_{th}$ by a zone selector 50. The zone selector can comprise, for example substantially conventional threshold circuitry for processing signals from the pressure sensors. For each pressure sensor providing a signal having a voltage magnitude exceeding $V_{th}$, the zone selector 50 provides a signal that directs cooled fluid provided by a cooled fluid source 52 through a means 53 that may comprise, for example, a manifold. The fluid flow in each zone may be controlled by a zone controller such as the zone controllers 55, each comprising, for example, a valve mechanism that initiates the flow of cooled fluid into the associated zone. This permits the provision of a separate, respective flow of cooled fluid into one or more zones of the cooling layer 30.

Alternatively, the fluid flow in each zone can be manually controlled by a caregiver. In this regard each zone in the cooling layer would have a known location with respect to the support surface. By visual inspection, the caregiver would note the location of weight-bearing areas known to be at risk for pressure injury and would activate the valve or valves necessary to initiate cooled fluid flow to the corresponding zones, thereby selectively cooling those specific skin areas at risk. Manual activation of zones is illustrated, in FIG. 5, by the MANUAL CONTROL input on each zone controller 55.

An advantageous result achieved by the invention as thus far described with reference to the preferred embodiment prevents general hypothermia and discomfort by cooling only those areas of a human or animal body that are in high pressure contact with the support surface 40. Since many bed-ridden patients who are at risk of pressure injury do not move around in bed on their own, automatic pressure sensing may be unnecessary, making manual control preferable. However, with spontaneous movement of the patient, automatic control as illustrated in FIG. 5 is incorporated into the invention.

Figure 6:
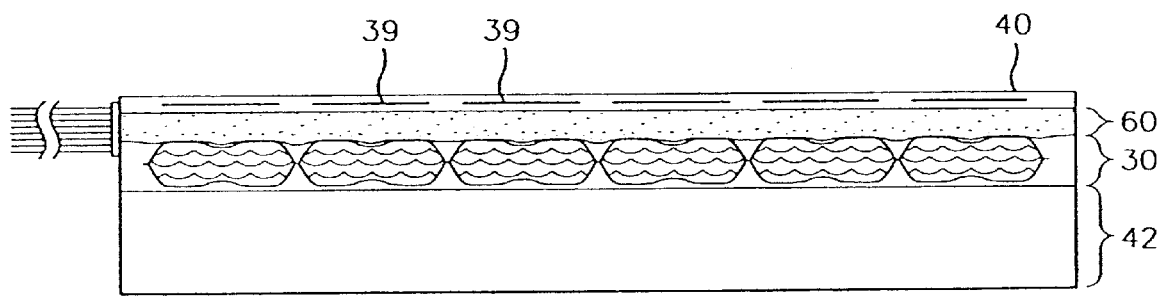
FIGS. 6 and 7 are partially schematic, longitudinal sectional illustrations of a variation of the first preferred embodiment.
Figure 7:
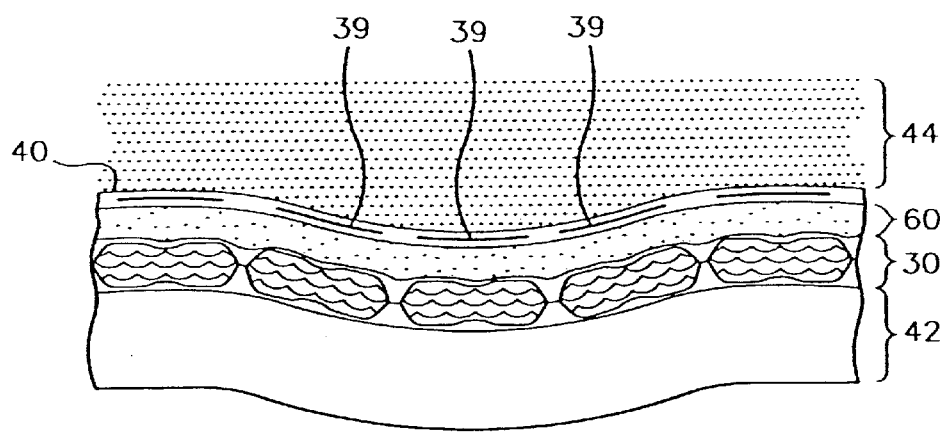

FIGS. 6 and 7 show a variation of the preferred embodiment illustrated in FIGS. 3 and 4, with the addition of a relatively thin layer 60 of thermally-conductive material disposed between the cooling layer 30 and the surface 40. The layer 60 is optional, and preferably comprises a pad of thermally conductive material which "evens out" the irregular upper surface that is an artifact of the thermo-formed channels in the water mattress embodying the cooling layer 30. Preferably the thermally-conductive material in the layer 60 may include, for example, a polymeric gel, water, or another fluid. Pressure sensors 39 may be disposed above, in, or below the thermally conductive layer 60.

Figure 8:
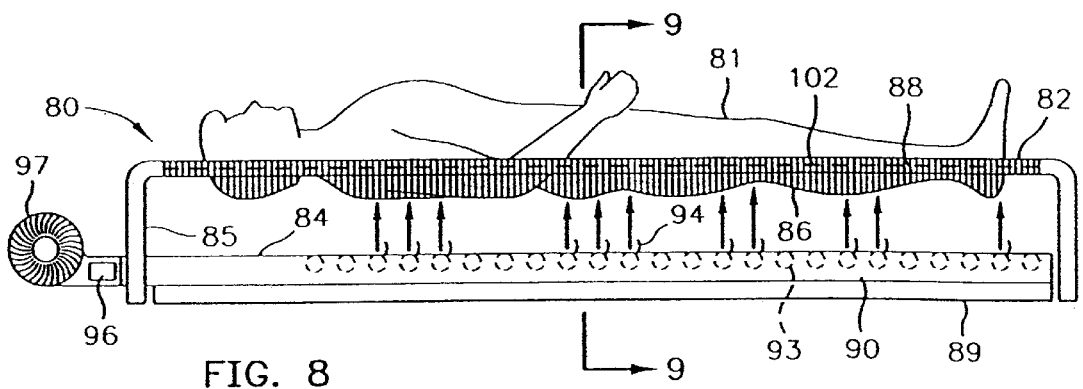
FIG. 8 is a partially schematic longitudinal section of a first alternate embodiment of the invention.
Figure 9:
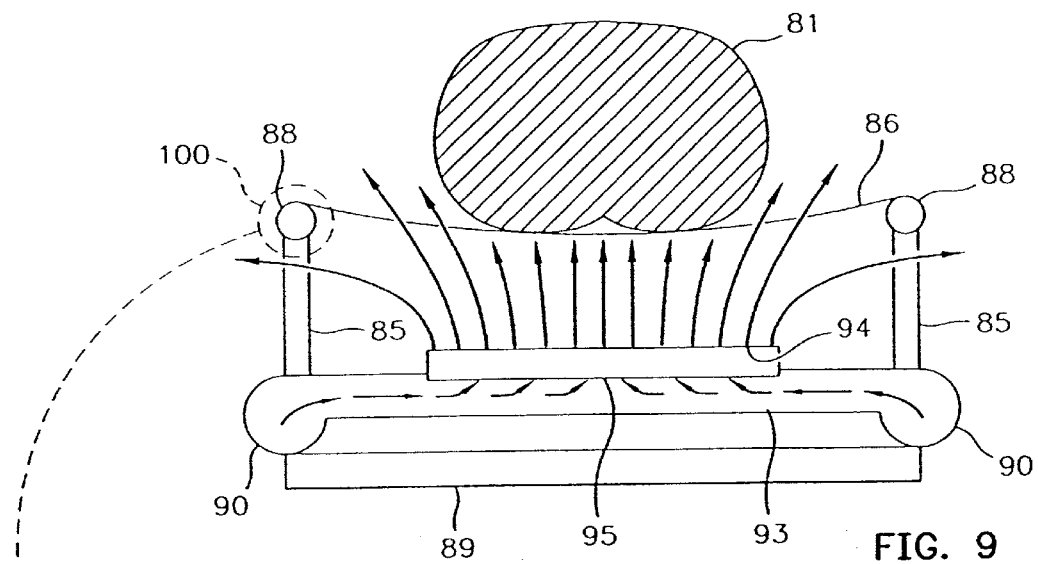
FIG. 9 is a longitudinal partially schematic cross-section of the first alternate embodiment at section 9—9 of FIG. 8.
Figure 10:
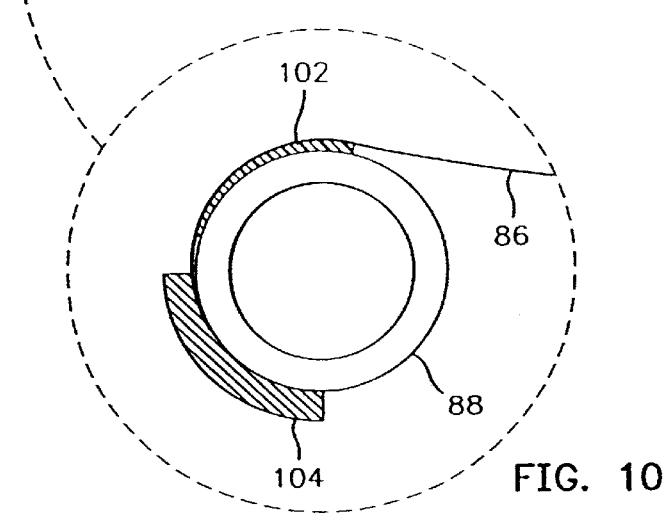
FIG. 10 is an enlargement of a portion of FIG. 9.

We refer now to FIGS. 8–10 which illustrate a first alternate embodiment of the invention. The first alternate embodiment of the invention is represented by an apparatus 80 having a patient support apparatus 82 which, in the figures is elongated to provide a cot-like structure that supports a supine person 81. It is to be understood that the first alternate embodiment is not intended to be limited strictly to support of a fully extended, reclining person, but is applicable as well to the support to less than all of a human or animal body. Disposed beneath the support structure 82 is a cooling layer in the form of a manifold plenum structure 84 that is divided into zones for selective cooling in accordance with principles already discussed in the exposition of the preferred embodiment.

The support apparatus 82 includes a frame 85 for supporting the apparatus, for example, on a floor or other support surface, and a mesh 86 extending between, and anchored to, elongated parallel anchoring pipes. 88. The manifold plenum structure 84 is supported on a base 89 and includes two parallel, separated longitudinal air plenums 90 and a plurality of air plenums 93 disposed transversely with respect to the elongated longitudinal air plenums 90. The longitudinal air plenums 90 communicate with the transverse air plenums 93 for conveyance of cooled air. One longitudinal air plenum 90 includes a means for receiving a cooled air stream from a source of pressurized cooled air including the air cooling means 96 and blower 97.

Each of the transverse air plenums 93 is disposed beneath a respective portion of the mesh 86. Manifestly, the mesh 86 comprises a support surface corresponding to support surface 40 discussed above, while the transverse air plenums 93 comprise a plurality of zones that are selectively controlled to cool elongated transverse portions of the mesh 86. Selective control of each air plenum is provided by an air jet slot valve 94 having a first, normally closed position covering an air jet slot 95, and a second, open position opening its associated air jet slot 95.

As the cross-sectional partially schematic drawing set forth in FIG. 9 illustrates, the flow of pressurized air travels through the longitudinal air plenums 90 and through all of the transverse air plenums 93, including the transverse air plenum 93 shown in FIG. 9. In FIG. 9, the transverse air plenum 93 is positioned beneath the buttocks of the supine person 81 and has been operated to have its air jet slot valve 94 open in order to direct a flow of cooled air upwardly toward the mesh 86. The flow of cooled air cools the mesh 86 and the weight-bearing area in the buttocks of the person 81 that exerts pressure on the mesh 86 at the cross-sectional location. The air introduced by an air jet slot 95 exits either from under the side and ends of the support apparatus 82, or through the mesh 86 (if the mesh is porous).

FIG. 10 is an enlarged illustration of a portion of the first alternative embodiment enclosed in the circle denoted by 100 in FIG. 9. The illustration is a mirror image of the corresponding section in the right-hand side of FIG. 9. As FIG. 10 illustrates, the mesh 86 is anchored to each of the elongated, parallel anchoring pipes 88 by a mesh anchoring flange 104 that is conventionally attached to the pipe 88 and which pinches the mesh 86 between itself and the pipe 88. Along a circumferential section of the pipe 88 that is not covered by the flange 104 there is disposed a pressure transducer 102 between the mesh 86 and the pipe 88. As a reference to FIG. 8 shows, there are a plurality of pressure transducers 102 distributed along the anchoring pipes 88 such that each transverse air plenum 93 is aligned with a respective one of a plurality of pressure transducers 102. Although not shown in FIGS. 8–10, pressure transducers can be arrayed in this or any suitable manner along one, or both, of the anchoring pipes 88.

In the first alternate embodiment illustrated in FIGS. 8–10, the patient 81 is supported by a mesh that is preferably a woven fabric of synthetic, natural, metal, or glass fibers, or a combination thereof. Preferably, but not necessarily, the mesh 86 has a loose weave so that air can pass through it. The transverse cooling zones are defined by the transverse air plenums 93 that are, preferably, periodically spaced along the longitudinal dimension of the supine patient beneath the mesh 86. Alternatively, the air plenums 93 can be arranged to form cooling zones of other shapes, such as a "checker-board" pattern. The air flow directed through the manifold plenum structure 84 can either be cooled or at room temperature. Of course, the air blowing on, or through, the mesh 86 cools the adjacent skin of the supine person 81. Each air jet slot valve that selectively activates a plenum may be embodied by, for example, a simple door hinged longitudinally on the outside surface of a transverse air plenum 93 to open and shut over a corresponding air jet slot. Many other air valving means are feasible.

The schematic layout of FIG. 5 embodies an architecture suitable for selectively controlling the air jet slot valves 94 of the first alternate embodiment. In this regard, each zone controller can comprise, for example, an activator such as an electro-mechanical solenoid that mechanically opens and shuts the valve, thereby selectively providing air to blow on a portion of the mesh 86.

As with the preferred embodiment, the zone to be cooled can be manually controlled by the caregiver by manual activation of a corresponding air jet slot valve 94. Optionally, the sensor/zone selector combination illustrated in FIG. 5 can be implemented using the structural elements illustrated in FIGS. 8–10. In this regard, each of the sensors 102 can comprise a piezoresistive pressure sensor.

Figure 11:
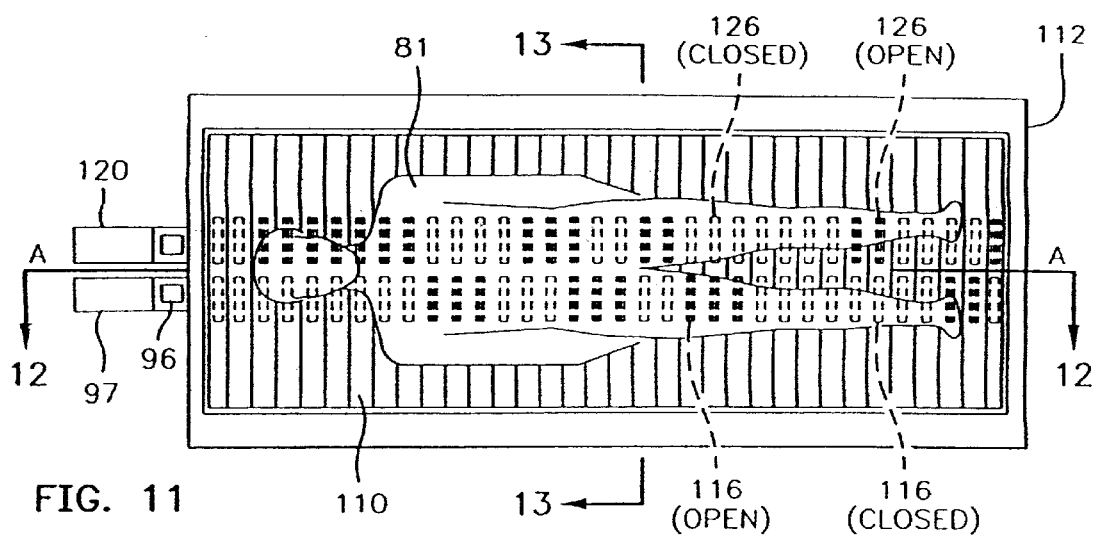
FIG. 11 is a top plan view of a second alternate embodiment of the invention.
Figure 12:
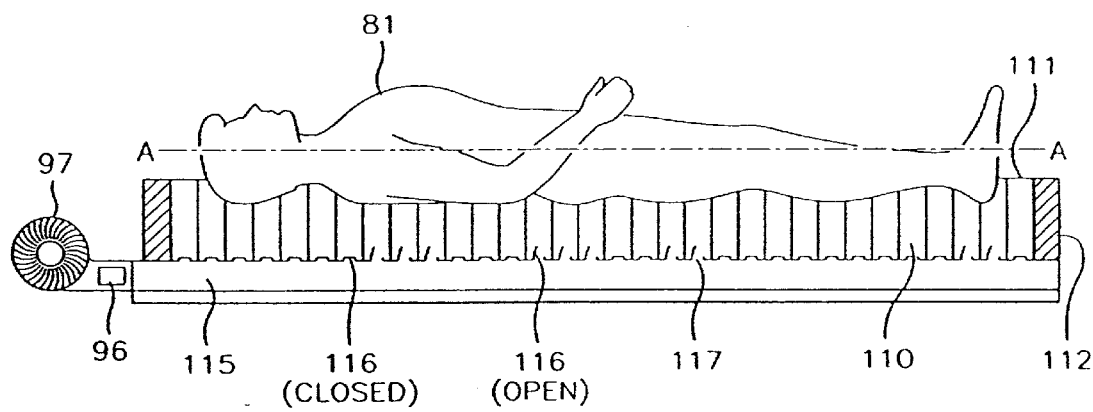
FIG. 12 is a longitudinal sectional, partially schematic view taken along 12—12 of FIG. 11.
Figure 13:
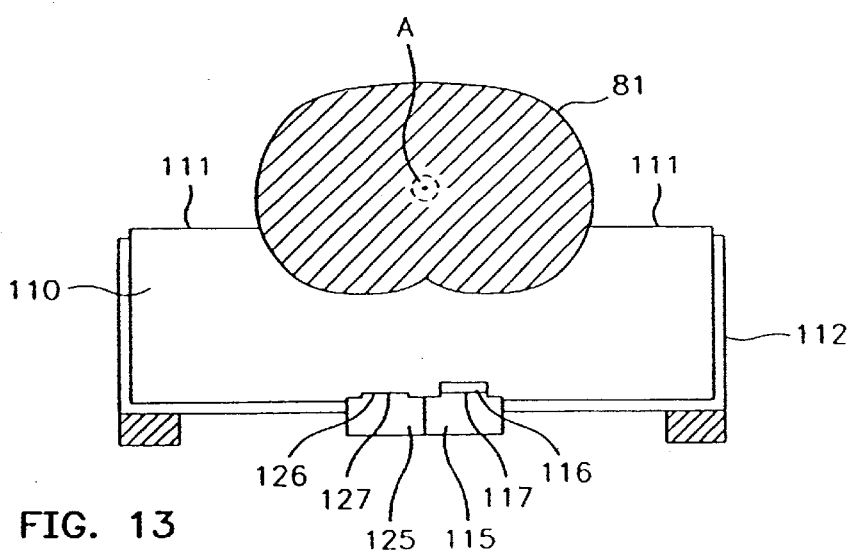
FIG. 13 is a cross sectional, partially schematic view taken along section 13—13 of FIG. 11.

Refer now to FIGS. 11, 12 and 13 in which a second alternative embodiment of the invention is illustrated. In these figures, a plurality of rectangular, inflatable air bladders is disposed in a sequential array. In this array, each air bladder is oriented in parallel with at least one adjacent air bladder, and transversely with respect to the longitudinal axis A—A of the supine person 81. Each of the air bladders 110 includes an upper surface 111, and the upper surfaces 111 of the air bladders 110 collectively form the surface that supports the supine person 81. Alternatively, the surface may comprise a thin layer of compliant heat-conductive material contiguous with the upper surfaces of the air bladder. Preferably, the rectangular air bladders 110 are supported in an open, five-sided rectangular frame 112. The air bladders 110 are made of flexible woven materials such as a synthetic fabric which may or may not be coated with a polymeric material, or bonded to a polymeric film.

A first single elongated plenum 115 that encompasses the length of the frame 112 receives a cooled air flow from 96, 97 and conveys it to the air bladders 110, each of which encompasses substantially the width of the frame 112. The first plenum 115 feeds each air bladder through an air jet slot 117. Each air jet slot 117 is controlled by an air jet slot valve 116 having an opened position, permitting cooled air to flow into, and circulate through, an air bladder 110, and having a closed position that prevents cooled air from flowing into the air bladder 110. Control of the air jet slot valves 116 can be as disclosed above in reference to the preferred and first alternate embodiments. Relatedly, the air jet slot valves 116 are preferably solenoid-driven with solenoid control provided either by manually operated or automatically controlled means. In this later regard, an array of thin film pressure sensors can be disposed in a single sheet across the upper surfaces 111 in such a manner as to align a sensor with each of the air bladders 110 for automatic control as illustrated above in connection with FIG. 5.

Each air bladder includes means for discharging air in a controlled manner, to allow continuous circulation of air within, and through, the bladder 110. The means for discharging air can include migration through a controlled weave porosity of the fabric, air vents, or an air return duct.

An air flow at higher temperature than the temperature of the cooled air flow delivered through the first plenum 115 is generated by a fan 120 and heating element 121. A second, single elongate plenum 125 receives the higher-temperature flow from 120, 121 and conducts it to the air bladders 110. The second plenum 125 is provided for heating, if needed, and for maintaining the inflation of air bladders not receiving cooled air. The second plenum 125 feeds each air bladder through an air jet slot 127 that is controlled by an air jet slot valve 126 having an opened position, permitting higher-temperature air to flow into, and circulate through, an air bladder 110, and having a closed position that prevents higher-temperature air from flowing into the air bladder 110. Control of the air jet slot valves 126 can be as disclosed above in reference to the preferred and first alternate embodiments. Relatedly, the air jet slot valves 126 are preferably solenoid-driven with solenoid control provided either by manually operated or automatically controlled means. In this latter regard, the array of thin film pressure sensors can be processed by a voltage threshold $V_{th}$, with a pressure sensor generating a voltage above this threshold in response to weight-bearing pressure, which will automatically close the air jet slot valve 126 and open the air jet slot valve 116, permitting cooled air to circulate into and through the air bladder. For pressures which do not cause the generation of voltage in excess of the threshold voltage, the air jet slot valves 116 would be closed, while the air jet slot valves 126 would be open. This reciprocal operation will maintain all air bladders at some predetermined state of inflation or distention in response to circulating air, thereby ensuring a uniform support of the body 81 across the surface that supports the body.

Obviously, many modifications and variations and many alternate embodiments may be made to this invention without departing from its spirit and scope which are limited only by the claims that follow.

We claim:

1. An apparatus for cooling a human or animal body, the apparatus comprising:
   a cooling layer having a plurality of zones;
   a support structure including a frame and a mesh supported by the frame, the mesh having a support surface disposed over the cooling layer
   each zone of the cooling layer being disposed for cooling a respective portion of the support surface;
   a plurality of sensors acting between the frame and the mesh; and
   a zone controller connected to the plurality of sensors and to the plurality of zones for operating one or more of the zones in response to signals produced by the sensors.

2. The apparatus of claim 1, wherein the cooling layer comprises a structure for circulating cooled air, the structure being partitioned into a plurality of plenums, each plenum for providing a flow of cooled air.

3. The apparatus of claim 1, each sensor of the plurality of sensors being substantially aligned with a respective zone of the plurality of zones.

4. The apparatus of claim 1, wherein the cooling layer includes a plenum structure for circulating cooled air.

5. The apparatus of claim 4, wherein the plenum structure includes a plurality of air plenums, each positioned with respect to a respective portion of the mesh and including an air jet opening for directing a flow of cooled air onto the respective portion of the mesh.

6. The apparatus of claim 5, the zone controller selectively operating air jet openings of a plurality of air plenums by opening and closing the air jet openings.

7. The apparatus of claim 6, wherein the plurality of sensors is disposed to sense pressure acting between the frame and the mesh, the zone controller responding to a pressure sensed by a sensor by opening an air jet opening of an air plenum positioned with respect to the respective portion.

8. The apparatus of claim 4, wherein:

the frame and the mesh form a cot-like structure; and the plenum structure includes at least one longitudinal air plenum and a plurality of transverse air plenums in communication with the at least one longitudinal air plenum.

9. The apparatus of claim 1, wherein each sensor of the plurality of sensors comprises a piezoelectric sensor.

* * * * *